United States Patent [19]

Roberts

[11] Patent Number: 4,901,577
[45] Date of Patent: Feb. 20, 1990

[54] APPARATUS FOR DETECTING SPLICES IN THE WEB OF A PRINTING PRESS

[75] Inventor: Christopher C. Roberts, Marion County, Ill.

[73] Assignee: World Color Press, Inc., Effingham, Ill.

[21] Appl. No.: 187,339

[22] Filed: Apr. 28, 1988

[51] Int. Cl.$^4$ .............................................. G01B 17/02
[52] U.S. Cl. ....................................... 73/600; 73/159
[58] Field of Search .................... 73/600, 599, 159; 340/675

[56] References Cited

U.S. PATENT DOCUMENTS

| | | | |
|---|---|---|---|
| 3,519,222 | 7/1970 | Nash et al. | 340/675 |
| 4,117,732 | 10/1978 | Brazhnikov | 73/599 |
| 4,446,735 | 5/1984 | Weilacher | 73/159 |
| 4,519,249 | 5/1985 | Hunt | 73/159 |

Primary Examiner—John Chapman
Attorney, Agent, or Firm—Gravely, Lieder & Woodruff

[57] ABSTRACT

The web in a high speed printing press passes between a transmitter and receiver, the former of which produces ultrasonic sound which the latter receives, after attenuation by the web, and the latter of which converts the sound into an oscillating electrical signal of corresponding frequency. This electrical signal, after being amplified and filtered, is impressed upon a peak detector and a comparator. The peak detector produces a constant potential equal to the amplitude of the peaks in the amplified signal, and this constant potential is reduced a predetermined proportion and is applied to the comparator as a reference potential. The comparator compares the reference potential with the amplified oscillating signal. The reference potential remains undisturbed even though the oscillating signal may momentarily drop due to the further attenuation of the sound caused by a splice moving through it. The comparator produces an oscillating signal when the peaks of the amplified signal rise above the reference potential, but when the peaks of the amplified signal drop below the reference potential as a result of further attenuation by a splice, the comparator creates a discontinuity in its oscillating signal. This discontinuity is detected and is utilized to trigger a marking device for imparting a suitable mark to the web both before and after the splice.

22 Claims, 3 Drawing Sheets

APPARATUS FOR DETECTING SPLICES IN THE WEB OF A PRINTING PRESS

BACKGROUND OF THE INVENTION

This invention relates in general to handling extended lengths of thin sheet material, such as paper, and more particularly to a device for detecting a splice or other variance in thickness of such material.

Most magazines and many other publications as well are printed on high speed offset presses. The typical press applies a succession of identical printed impressions to a continuous web of paper which passes through the press at a high velocity - often exceeding 1000 ft/min. In addition to the print stands where the ink is actually applied to the web, the typical press includes a dryer which dries the ink, and a former board over which the web is folded and perhaps combined with another web such that the printed impressions on the two webs are in registration. A cutter exists at the end of the press, and here the combined webs are severed between their successive printed impressions to provide individual signatures which are stacked one upon the other. These signatures are later combined with other signatures derived from other runs on the same press or from runs on a different press, and the combined signatures are bound together to produce the magazine or other publication.

The web pays off of a roll of paper large enough to last for 20 to 30 minutes, notwithstanding the high velocity. To avoid rethreading the web once the roll from which it derives is depleted, i is the common practice to splice the end of the web from a depleted roll to the beginning of the web from the new roll. Thus, no interruption in the operation of the press occurs, other than perhaps a reduction in the web velocity to permit the formation of the splice.

The splice advances through the press and rarely falls between printed impressions. But to allow a signature containing a splice to be embodied in an actual magazine is totally unacceptable. The typical procedure for eliminating signatures containing splices involves simply placing a pencil against the web, normally where the web passes over the former board, when splice advances through the press. The splice falls within the group of marked signatures, which usually amount to about 100, and by discarding the entire group, one is assured of eliminating that one signature containing the splice. Many other signatures are eliminated as well-needlessly.

Heretofore, optical sensors have been installed along the web paths of printing presses to detect splices, but these devices have not proved to be very satisfactory. For example, fluctuations in the distance of the web from the sensor will on occasion trigger such a device, providing a false indication of a splice. Being sensitive to the thickness of the paper, these sensors must be adjusted to accommodate webs of varying thickness, and this represents an additional inconvenience.

The splice detector of the present invention directs sound through a rapidly moving web. While the web attenuates the sound waves, a splice in the web will attenuate the sound waves still further, at least for an instant, and this further attenuation is sensed and correlated to the web which is marked for a short distance ahead of the splice and likewise for a short distance beyond the splice. The signatures which bear the markings are thereafter removed, but these signatures are quite few in number. Of course, the splice is within one of those signatures. The device automatically compensates for varying thickness of paper.

DESCRIPTION OF THE DRAWINGS

In the accompanying drawings which form part of the specification and wherein like numerals and letters refer to like parts wherever they occur.

DETAILED DESCRIPTION

Figure 1:
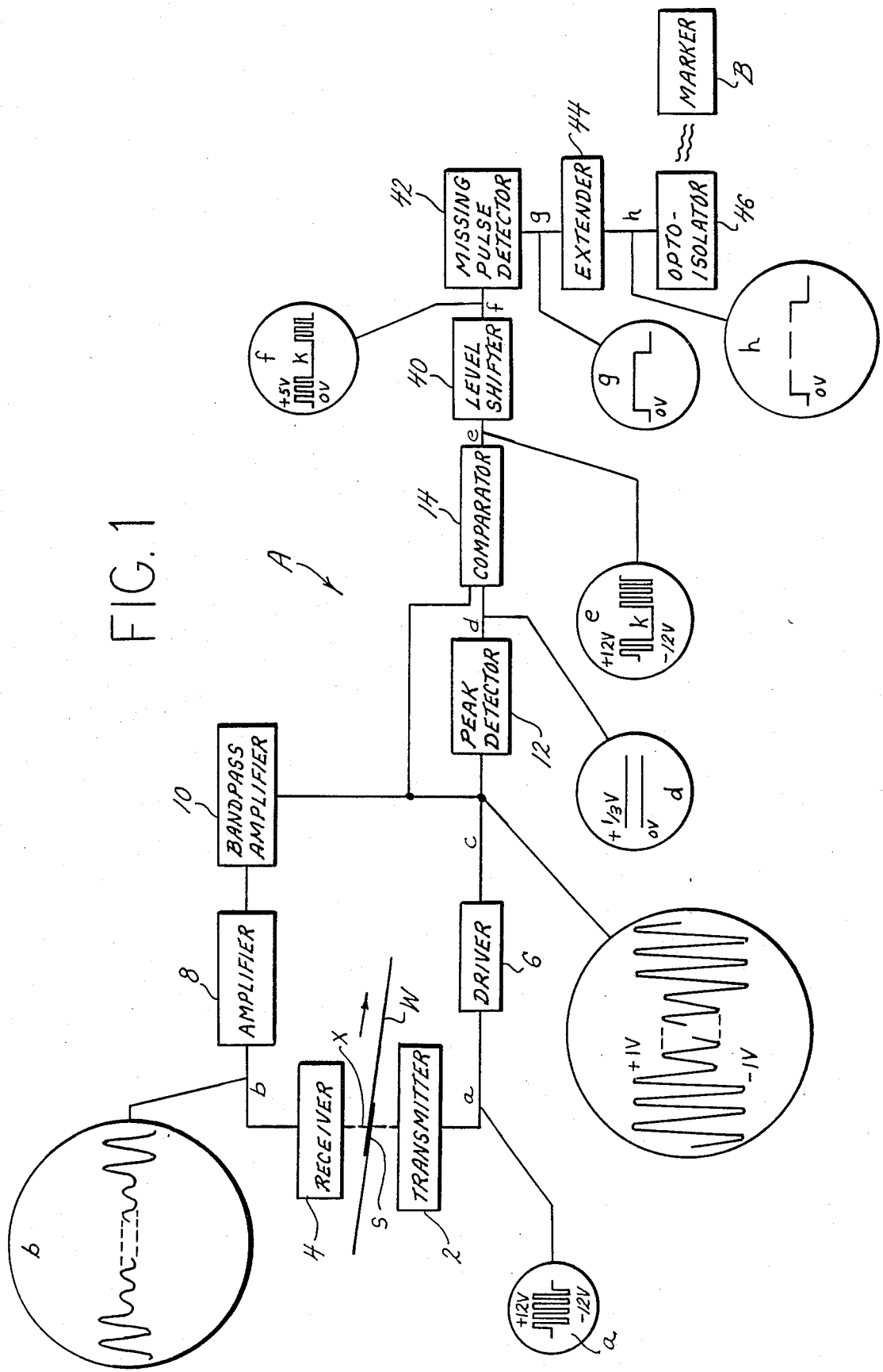
FIG. 1 is a block diagram of a splice detecting apparatus constructed in accordance with and embodying the present invention and further depicting the form of the electrical signals at various places in the apparatus.

Referring now to the drawings (FIG. 1), a splice detecting apparatus A is located along a path occupied by a web w as the web w travels through a printing press. The apparatus A continuously monitors the thickness of the web w, and when it detects an abrupt increase in thickness, it produces a signal which causes a marking device B to apply a marking to the web w. The web w, while constituting an extended length of paper, is not continuous in the sense that it possesses uniform thickness throughout its length. Instead, it comprises successive sections which are joined together at splices s. Each splice s constitutes nothing more than a short overlap between the leading and trailing sections, with of course a glue between the overlapping portions to hold them together. Thus, at each splice s the web w possesses twice its normal thickness, and also includes a film of glue which further changes the character of the web w at that location.

The printing press on which the splice detecting apparatus A and marking device B are installed applies successive printed impressions, which are identical, to the web w, and thereafter dries the ink that forms those impressions. The web w then passes over a former board where it is folded, and the folded web w is cut into signatures between its printed impressions. The signatures are thereafter combined with other signatures and the combined signatures are bound together to produce a magazine or other publication. Of course, a magazine containing a signature through which a splice s extends is totally unacceptable, an therefore each splice s must be located, so that the signature in which it exists can be discarded. While the detecting apparatus A may be located generally anywhere along the web w, it is preferably located slightly ahead of the former board where the web w is folded. Preferably, the marking device sprays ink onto the web w for a short duration, and where the detecting apparatus A is located ahead of the former board, the marking device may be at the former board with its ink jet directed toward the fold as the fold develops over that board. In any event, the detecting apparatus A and the marking device B are so correlated with each other and with the web w that the mark applied by the marking device B spans the splice s sensed by the apparatus A, extending longitudinally along the web a short distance ahead of the splice s and a short distance behind the splice s.

The detecting apparatus A includes an ultrasonic transmitter 2 which is presented toward one face of the web w and ultrasonic receiver 4 which is presented toward the opposite face of the web w (FIG. 1). Moreover, the transmitter 2 and receiver 4 are presented toward each other and would be exposed to each other were it not for the presence of the web w between them. Stated differently, the transmitter 2 and receiver 4 are aligned along a line x which intercepts the web w, and that line should be oblique to the web w in the direction of web advance. Indeed, the angle between the line x and the plane of the web w is such that a gap of about ⅜ in. exists between the web w and the upstream edge of the transmitter 2, and the distance between the web w and the downstream edge of the receiver 4 is likewise about ⅜ in.

The ultrasonic transmitter 2 produces sound at about 40 KHz, which is beyond the audible range, and directs the ultrasonic sound waves so produced toward the receiver 4 generally along the line x. While the waves pass through the web w, they are attenuated by it.

Figure 2:
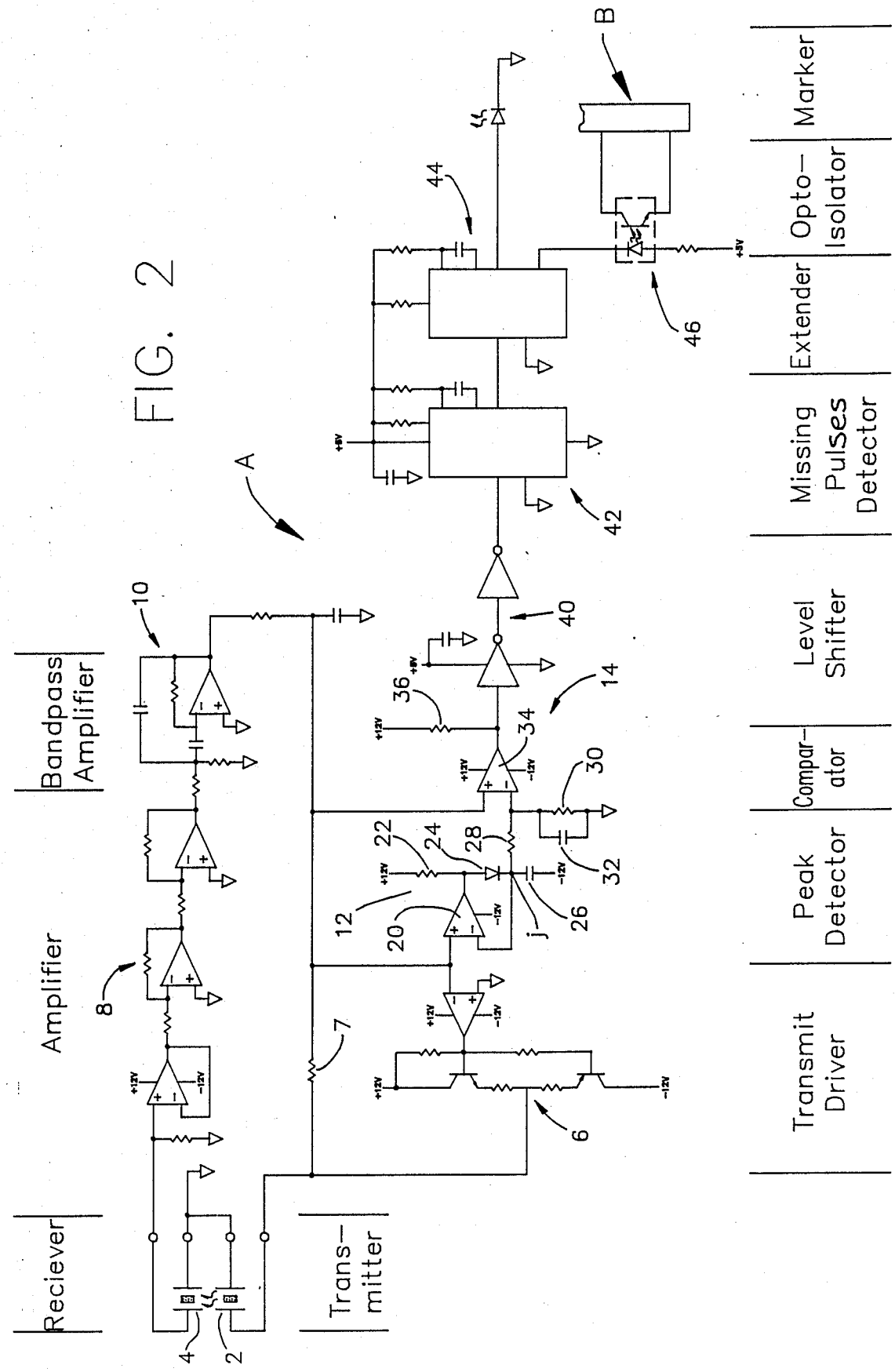
FIG. 2 is a schematic view of the electrical circuitry for the splice detecting apparatus.

Actually, the transmitter 2 responds to a transmit driver 6 to which the transmitter 2 is electrically connected. The driver 6 produces a square wave signal a (FIG. 1) which oscillates between equal positive and negative amplitudes at the frequency for the ultrasonic transmission through the web w, the preferred frequency being about 40 KHz. The transmit driver 2 contains an operational amplifier, two transitors, and several resistors all organized and connected as indicated in the electrical schematic (FIG. 2). The collectors of the operational amplifier are connected between positive and negative direct current sources which are maintained at voltages which correspond to the voltages in the oscillating signal a which it produces. For example, when the driver 6 is connected between current sources maintained at +12 V DC and at −12 V DC, the square wave signal a produced by the driver 6 and delivered to the transmitter 2 will oscillate between +12 V and −12 V at 40 KHz. Through other components yet to be described, the driver 6 is connected by a loop back to the receiver 4, and this enables the driver 6 to self-oscillate once an initial oscillatory signal develops in the loop between the receiver 4 and the driver 6. The driver 6 contains a feedback resistor 7 which enables the driver 6 to act as an oscillator and thus develop the initial oscillatory signal which the driver perpetuates.

Turning now to the receiver 4, it is in essence a microphone that is sensitive to a narrow range of frequencies around 40 KHz. The sound of course plots as a sine wave, and the receiver 4 does nothing more than to convert this sound into a corresponding electrical signal b which plots as a sine wave of equivalent frequency. The electrical signal b, however, is quite weak.

This weak signal b produced by the receiver 4 is delivered to an amplifier 8 to which the receiver 4 is connected, and here the signal b is amplified substantially. The amplifier 8, which amplifies over a wide band of frequencies, may have a gain of 9.5 at the frequency of the signal b.

The amplifier 8 is in turn connected to a bandpass amplifier 10 which amplifies the signal b still further, perhaps by a gain of 3. The bandpass amplifier 10 is tuned to the dominant frequency of the signal b, that is 40 KHz, it having a bandwidth of about 20 KHz. It attenuates all frequencies outside of this bandwith and thus rejects unwanted frequencies which might cause the detecting apparatus A to erroneously indicate the presence of a splice 3. Thus, the amplifier 8 together with the bandpass amplifier 10 produce an amplified signal c which possesses all of the characteristics of the signal b, except unwanted noise, and of course its amplitude is greater. Indeed, the amplified signal c may have an amplitude ranging between +1 V and −1 V, but its actual amplitude depends on the attenuation caused by the web w, and that to a large measure depends on the thickness of the web w.

One component to which the amplifier 10 directs the signal c is the transmit driver 6 which converts the signal c into the square wave signal a of equivalent frequency, but at an amplitude of ±12 V. The square wave signal a in turn drives the transmitter 2 which produces the 40 KHz sound which is thence converted into the 40 KHz electrical signal b. Thus, the transmit driver 6 is self-oscillating, its frequency being established by the ultrasonic receiver 4 which is sensitive to only a narrow range of frequencies around 40 KHz.

The amplified signal c delivered by the bandpass amplifier 10, not only provides the stimulus that sustains the transmit driver 6, but it further passes on without alteration to a peak detector 12 and also to a comparator 14. Indeed, the two amplifiers 8 and 10 boost the relatively weak signal b derived from the receiver 4 to the signal c that is useful by the peak detector 12. The comparator 14 in essence compares the signal c with a reference potential d produced by the detector 12, and to this end the comparator 14 is also connected to the detector 12.

Considering the peak detector 12 first, it includes (FIG. 2) an operational amplifier 20, which is a basic electronic component, having a positive input terminal and a negative input terminal as well as a single output terminal. The positive input terminal is connected to the bandpass amplifier 10, and thus at this location the amplified sinusoidal signal c representing the ultrasonic sound is impressed on the detector 12. Hence, the voltage at the input terminal fluctuates at the amplitude and frequency for the signal c, which could be typically ±1 V at 40 KHz. The peak detector 12 also includes a resistor 22, a diode 24 and a capacitor 26 connected in series in that order between the positive and negative power sources which in this instance are +12 V DC and −12 V DC respectively. When the diode 24 conducts, this series connection produces a typical RC circuit in which the potential at point j between the capacitor 26 and diode 24 builds up. The diode 24 is oriented with its anode presented toward the resistor 22 and its cathode presented toward the capacitor 26. The negative input terminal of the operational amplifier 20 is connected to the cathode of the diode 24, while the output terminal of the operational amplifier 20 connected to the anode of the diode 24. Moreover, one of the pins of the operational amplifier 20 is left open, while the other is connected to the negative power source which in this instance is maintained at −12 V DC.

The peak detector 12 produces a peak level voltage d' (FIG. 3) which exists at a point j between the capacitor 26 and diode 24, that is at the negative input terminal to the operational amplifier 20, and this voltage d' normally equals the voltage for the maximum positive amplitude of the signal c derived from the bandpass amplifier 10. Thus, if the amplifier 10 produces a sinusoidal signal of ±1 V, point j will exist at +1 VDC. Even so, the voltage d' at point j does not immediately rise to the peak level, for point j is in effect within an RC circuit formed by the resistor 22 and the capacitor 26. This circuit of course possesses a time constant.

The peak detector 12 further includes series-connected resistors 28 and 30, with the latter being connected to ground and shunted by a capacitor 32. It is through the resistor 28 that the output of the peak detector 12 is directed to the comparator 14 as the reference potential d. Actually, the resistor 28 creates a voltage drop so that the reference potential d impressed on the comparator 14 is less than the peak voltage d' produced in the peak detector 12. The resistors 28 and 30 are selected so that the voltage between the two, that is the reference potential d which is maintained at the comparator 14, is about one-third the peak voltage d'.

Figure 3:
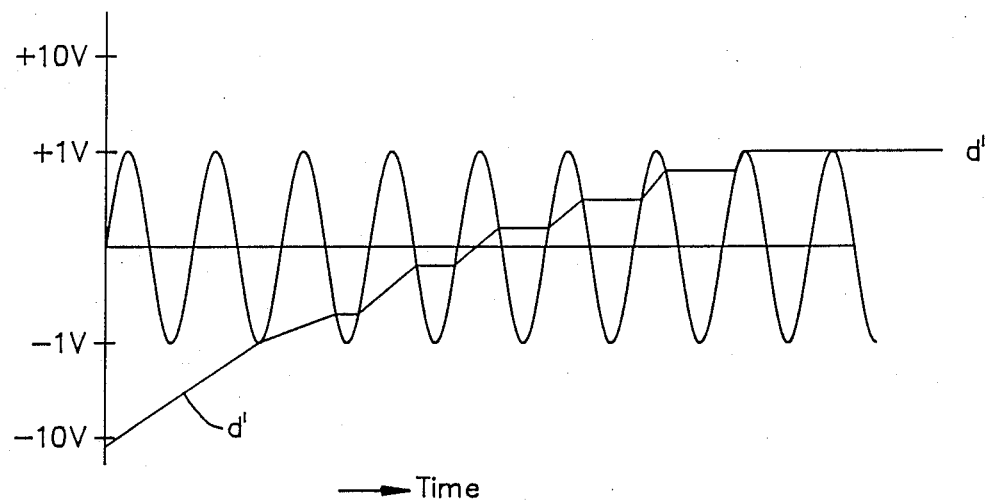
FIG. 3 is a plot showing a typical signal derived from the band pass amplifier, and the development of a reference potential in the peak detector.

When the apparatus A is placed in operation, voltage at point j is $-12$ VDC, the same as on the other side of the capacitor 26. But the diode 24 is forwardly biased by the voltage impressed on it through the resistor 22, and as a result current flows through it, and indeed the capacitor 26 and resistor 22 are in series between the $-12$ V and $+12$ power sources, thus creating a simple RC circuit. The voltage at point j thus rises with time and will exceed the minimum voltage for the signal c which is impressed at the input terminal of the operational amplifier 20, that is to say it will rise to a level greater than one of the minimum peaks. Of course the voltage at point j equals and indeed is the voltage at the negative input terminal of the operational amplifier 20. The amplifier 20 is such that when the voltage at its negative input terminal is less than the voltage at its positive input terminal, it does not conduct. However, once the voltage at the negative input terminal equals or exceeds the voltage at the positive input terminal, the operational amplifier 20, which is also connected to the negative power source, causes the voltage of the negative power source, $-12$ VDC in this instance, to appear at its output terminal. Since the output terminal of the operational amplifier 20 is connected directly to the anode of the diode 24, the anode is reversed biased at $-12$ VDC and hence fails to conduct. In other words, the capacitor 26 is isolated from the resistor 22 and the positive power source, and the build up of the electrical potential d' at point j momentarily ceases. Indeed, it is halted until the voltage at positive input terminal of the operational amplifier 20 rises to that of the negative terminal, which occurs within less than one-half of a full cycle for the signal c (FIG. 3). At this instant the operational amplifier 20 removes the $-12$ VDC reverse bias from the anode of the diode 24, so the diode 24 becomes forwardly biased and again conducts, allowing for a further buildup of the voltage d' on the capacitor 26, that is at point j. The foregoing switching occurs with each cycle of the signal c applied at the input terminal, and eventually the voltage at point j reaches the peak positive voltage of the signal c. When this occurs, the voltage at the negative input terminal for the operation amplifier 20, in effect, never exists at a level below the voltage at the positive terminal, which of course has the signal C applied to it, and as a consequence the negative voltage of the power source exists at the output terminal and the anode of the diode 24. Thus, the diode 24 remains reversely biased and fails to conduct. The voltage d' at point j, on the other hand, remains generally constant at the peak voltage of the signal c, that is the maximum for the positive amplitude of the signal c, which typically could be 1 V. The resistors 28 and 30 reduce the peak voltage d' about one-third, creating the reference potential d which is monitored by the comparator 14.

The web w, except at the regions of the splices s within it, is of generally uniform thickness and consistency throughout its length, and while it attenuates the ultrasonic sound waves produced by transmitter 2, the attenuation is constant and the receiver 4 produces a signal b of generally uniform amplitude. The signal c which appears at the peak detector 12, that is at the positive input terminal of its operational amplifier 20, being merely an amplification of the original signal b, likewise has peaks of uniform magnitude. When a splice s passes between the transmitter 2 and receiver 4, the sound reaching the receiver 4 is attenuated still further, albeit for an instant, and while this lessens the magnitude of the peaks in the signal c to the peak detector 12, the voltage d' at the point j remains constant owing to the stabilizing effect of the capacitors 26 and 32. Since reference potential d follows the voltage d' at the point j, it too remains essentially constant during the momentary attenuation caused by splice s.

The comparator 14 essentially comprises an operational amplifier 34 (FIG. 2) having its positive input terminal connected to the bandpass amplifier 10 and its negative input terminal connected between the resistors 28 and 30 of the peak detector 12. Thus, the amplified sinusoidal signal c that represents sound waves passing through the web w is impressed on the positive input terminal for the operational amplifier 34 of the comparator 14, while the reference potential d is impressed on the negative input terminal. The former possesses peaks, while the latter constitutes a constant or DC voltage, which while positive, is about one-third the magnitude of the peaks in the signal c. The collectors of operational amplifier 34 are connected between the positive and negative power source, and the operational amplifier 34 produces at its output terminal a square wave signal e which alternates between the extremes of the power source to which the collectors are connected, that is between $\pm 12$ V. Actually, the operational amplifier 34 produces at its output terminal a positive voltage whenever the voltage on its positive input terminal exceeds the voltage at its negative input terminal, and conversely produces at its output terminal a negative voltage whenever the voltage at the input terminal is less than the voltage at the positive input terminal, and those voltages which appear at the output terminal correspond to the voltages impressed upon the operational amplifier 34 by the power source. In other words, for each peak in the amplified signal c that is above the reference potential d $+12$ V appears at the output terminal of the amplifier 34 and for each negative peak in amplified signal $-12$ V appears at the output terminal. The result is the square wave signal e at the output terminal for the operational amplifier 30, with that signal possessing the same frequency as the original signal b and the amplified signal c.

In addition to the operational amplifier 34, the comparator 14 includes a pull up resistor 36 connected between the positive power source and the output terminal of the operational amplifier 34. The arrangement appears in the electrical schematic (FIG. 2).

Normally, the sinusoidal signal c supplied to the comparator 14 has positive and negative peaks of constant amplitude, for this signal of course represents the movement of the generally uniform portion of the web w through the space between the transmitter 2 and receiver 4. The comparator 14 transforms this signal into the square wave signal e of equivalent frequency, with that signal fluctuating between ±12 V. However, when a splice s passes between the transmitter 2 and receiver 4, the attenuation caused by it in the sound is enough to reduce the amplitude of the peaks in the amplified signal c to less than one-third of its original value, although of course the frequency remains unchanged. As a result the entire amplified signal c remains below the reference potential d, and the output signal e of the comparator 14 remains at the negative potential for the duration of the splice s. This produces a discontinuity or gap k (FIG. 1) in the square wave signal e normally present at the output terminal for the operational amplifier 30 of the comparator 14.

Next comes a level shifter 40 which receives the signal e produced at the output terminal of the operational amplifier 30 for the comparator 14 and changes it to another signal f of different voltage level. The level shifter 40 converts the positive output excursion of the signal e produced by the comparator 14 to a lesser, yet positive, voltage and the negative execursion to no or zero volts. Typically, the 12 V excursion in the signal e appears as +5V in the signal f, while the −12 V excursion in the signal e appears as 0 V in the signal f. Of course the signal f tracks the signal e and thus possesses the same frequency and contains a gap k each time a splice s passes between the transmitter 2 and receiver 4, but that gap k, instead of being −12 V, will be 0 V.

The level shifter 40 includes two 1489 line receivers organized and connected as illustrated in the schematic drawing (FIG. 2).

Beyond the level shifter 40 lies a missing pulses detector 42 which is designed to detect a gap k with the signal f emanating from the level shifter 40. That signal, it will be recalled oscillates at the frequency of the transmitter 2 except for the gap k produced by a splice s in the web w. Then it merely remains at zero volts. The missing pulses detector 42 contains a standard electronic circuit, known as a one-shot, as well as resistors and capacitors, all connected as illustrated in the electrical schematic (FIG. 2). The output of the missing pulses detector 42 remains at 0 V when the detector 42 is subjected to a succession of pulses at the frequency of the original signal b, so the pulses in the signal f derived from the level shifter 40 do not cause the detector 42 to deviate from 0V. Indeed, each pulse retriggers the one shot of the detector 42, causing it to remain at 0V at its output terminal. However, when a voltage pulse is not received within a particular span of time, the detector 42 produces at its output terminal a signal in the form of direct current voltage g which remains for the remaining duration of the absence of pulses, but disappears once the pulses resume in the signal f. In this case the one shot circuit of the missing pulses detector 42 is set such that it produces a signal when square wave signal f remains at 0 volts long enough for ten pulses to otherwise occur. In other words, if the signal f from the level shifter 40 contains a gap k that would otherwise hold ten pulses, the one shot circuit in the missing pulse detector 42 will provide a voltage g which will endure until the oscillating square wave signal f from the level shifter 40 resumes. The gap k in the square wave signal f of course results from a splice s passing between the transmitter 2 and the receiver 4, so the missing pulses detector 42 itself produces a pulse or voltage g which is longer in duration than the pulses of the signal f, but nevertheless is short enough to be characterized as a pulse.

The missing pulses detector 42 is connected to an extender 44 which in effect extends any pulse or voltage g derived from the missing pulses detector 42, indeed long enough to trigger the marker B. In this instance, the extender 44 in response to a pulse or voltage g from the missing pulses detector 42 produces a steady voltage h having a duration of about one second. The extender 44 likewise comprises a one shot circuit as well as resistors and a capacitor, all connected together as indicated in the electrical schematic (FIG. 2).

The extender 44, while it triggers the marking device B, is not connected directly to it, but instead the two are connected through an opto-isolator 46. The opto-isolator 46 merely provides optical isolation between the marking device B and the circuitry of the splice detecting apparatus A so that current surges in the marking device B do not damage the splice detecting apparatus A.

The marking device B preferably contains a nozzle which is directed at the web w where the web w passes over a former board and acquires a fold. When triggered, it sprays ink on the web w. When the web w is folded and converted into signatures, this ink will appear on the splines of several successive signatures. A delay may be incorporated into the marking device B to compensate for the time that it takes a splice on the web w to move from the receiver 4 of the splice-detecting apparatus A to the marking device B.

The typical printing press stacks the signatures at its very end, and within any stack, the marked signatures are clearly discernible by the contrasting appearance of the splines in the stack. These signatures, which are few in number, perhaps six or seven, are withdrawn from the stack, and within this group of marked signatures lies the splice.

Since the reference potential d produced by the peak detector 12 is proportional to the amplitude of the peaks in the signal c that is delivered to the comparator 14, it rises or drops with changes in the amplitude of the signal c. Those rises or drops would be occasioned by a change in the thickness of the web w. Thus, no special adjustments are required when the paper thickness is altered.

OPERATION

In the operation of the splice detecting apparatus A, the transmitter 2 produces ultrasonic sound waves having a frequency of about 40 KHz, with these waves being directed to the receiver 4 which is tuned to a bandwidth that embraces the 40 KHz. The web w passes between the transmitter 2 and receiver 4 and this attenuates the sound. Since the web posseses uniform thickness and density, except for its splices s, the attenuation is uniform, except of course when a splice s passes between the transmitter 2 and receiver 4. This event, which is of very short duration, produces an even greater attenuation. While the duration of the lesser attenuation may be short, it still is of significantly greater duration that the interval between successive sound waves produced by the transmitter 2, which interval is 1/40,000 sec.

The receiver 4 produces an electrical signal b, sinusoidal in nature, which is merely the electrical equivalent of the attenuated sound waves that pass through the web w. The amplifier 8 amplifies this signal 9.5 times, producing another sinusoidal signal, which in turn is amplified another 3 times by the bandpass amplifier 10, resulting in the amplified signal c. Being confined to a narrow frequency band centered at 40 KHz, the amplifier 10 eliminates many extraneous frequencies or noise that may exist in the prior signals, so the signal c produced by it electrically represents the sound that passes through the web w.

The sinusoidal signal c from the bandpass amplifier 10 sustains the transmit driver 6, enabling it to produce the square wave signal a with which the transmitter 2 converts into the ultrasonic sound that is transmitted to and through the web w.

The signal c from the bandpass amplifier 10 enters the peak detector 12 and the comparator 14. The peak detector converts this sinusoidal signal c into constant voltage d' equalling the maximum positive amplitude of the signal c, and this constant voltage d' remains at the amplitude of the signal, even when the signal c undergoes a momentary attenuation, as will occur when a splice s passes between the transmitter 2 and receiver 4. The constant voltage d' exists on one side of the resistor 28, but the resistors 28 and 30 reduces it, so that between the resistors 28 and 30 the voltage d' manifests itself as the reference potential d which is approximately one-third the maximum amplitude of the signal c. The latter reference potential d is impressed upon the comparator 14 which compares it with the sinusoidal signal c from the bandpass amplifier 10.

The comparator 14 produces a square wave signal e of ±12 V at the frequency of the signal c, at least as long as the peak amplitude of the signal c remains above the reference potential d impressed on the comparator 14. This condition of course exists as long as the uniform portion of the web w passes between the transmitter 2 and receiver 4. But once the splice s appears, the signal c will momentarily drop such that its peak amplitude is less than the reference potential d impressed on the comparator 14, and when this occurs, the signal e produced by the comparator 14 drops to −12 V and remains there for the duration of the interruption caused by the splice s, that is for as long as the peak amplitude of the signal e remains below the constant potential d. In short, the passage of a splice s between the transmitter 2 and the receiver A produces a gap k in the signal e.

The level shifter 40 merely transposes the peaks of the square wave signal from +12 V and −12 V to +5 V and 0 V, respectively, thereby producing another signal f having the latter extremes. All discontinuities in the signal e, that is to say the gaps k, pass through the level shifter 40 and appear as gaps k in the signal f.

The missing pulse detector 42 receives the square wave signal f from the level shifter 40, and as long as the signal f remains in its square way pattern, the missing pulse detector 42 produces at its output a signal of 0 V. However, the missing pulses detector 42, as its name implies detects missing peaks or gaps k in the square wave signal f, and whenever a predetermined number of cycles or pulses fail to appear in the signal f, the missing pulses detector 42 produces a potential g or pulse which exists for as long as the square wave signal is absent, which is of course for the remaining duration of the gap k. The predetermined number of cycles or pulses should not in time exceed the time required for the splice s to pass between the transmitter 2 and the receiver 4.

The extender 44 detects any pulse emitted by the missing pulses detector 42 and extends it into a constant voltage h extended duration, typically one second, which is long enough to trigger the marking device B, which it does through the opto-isolator 46. The marking device B sprays ink into the web for a short distance before the splice s and a short distance behind the splice s, so the location of the splice s is easily identified.

This invention is intended to cover all changes and modifications of the example of the invention herein chosen for purposes of the disclosure which do not constitute departures from the spirit and scope of the invention.

What is claimed is:

1. An apparatus for detecting within a generally uniform sheet material of extended length that moves along a path, a variation, such as a splice, in the otherwise uniform sheet material, said apparatus comprising: transmitting means for generating a sound along the path opposite one face of the moving sheet material; receiving means located along the path opposite the other face of the moving sheet material for converting the sound, after it passes through the sheet and is attenuated thereby, into an oscillating electrical signal of corresponding frequency, whereby the sound passing through the generally uniform of the sheet material will create within the oscillating signal a succession of peak-shaving a generally uniform portion magnitude, whereas the sound passing through the variation will create within the oscillating signal peaks of a different magnitude; amplifier means for amplifying the oscillating signal produced by the receiving means so as to provide an amplified signal likewise having peaks of a generally uniform magnitude representing the uniform portion of the sheet material and peaks of a different magnitude representing the variation; detector means connected to the amplifying means for converting the amplified signal into a generally constant reference potential which is different from, yet proportional to, the magnitude of the generally uniform peaks in the amplified signal; and comparing means connected to the amplifying means and the detector means for comparing the amplified signal with the reference potential and for indicating when the magnitude of the peaks in the amplified signal undergoes a change with respect to the reference potential, whereby the presence of a variation in the moving sheet material is detected.

2. The apparatus according to claim 1 wherein the comparing means produces an output signal comprising a succession of pulses corresponding in frequency to the amplified signal when the amplified signal constitutes a succession of uniform peaks greater in magnitude than the reference potential and a discontinuity when the amplified signal has peaks which are of a magnitude less than the reference potential.

3. The apparatus according to claim 2 and further comprising means for detecting discontinuities in the output signal of the comparing means.

4. The apparatus according to claim 3 wherein the means for detecting discontinuities in the output signal of the comparing means produces a pulse when a discontinuity is detected.

5. The apparatus according to claim 1 and further comprising driver means connected between the amplifying means and the transmitting means for producing pulses at a frequency corresponding to that desired for the sound produced by the transmitting means, the driver means being sustained by the amplified oscillating signal from amplifying means.

6. The apparatus according to claim 1 wherein the detecting means produces and sustains a generally constant potential corresponding to the magnitude of the uniform peaks and further derives the reference potential from the potential so produced.

7. The apparatus according to claim 6 wherein the peak detector comprises a first resistor, a diode and a capacitor connected in that order in series between a positive voltage source and a negative voltage source, with the anode of the diode being presented toward the resistor; an operational amplifier having positive and negative input terminals and an output terminal, the positive input terminal being connected to the amplifying means so that the oscillating signal is impressed upon it, the negative input terminal being connected to the cathode of the diode and the output terminal being connected to the anode of the diode; and a second resistor connected between the cathode of the diode and the comparator.

8. The apparatus according to claim 7 wherein the comparing means comprises an operational amplifier having a positive input terminal, a negative input terminal and an output terminal, and wherein the positive input terminal is connected to the amplifying means so that the amplified oscillating signal is impressed on it and the negative input terminal is connected to the second resistor of the detecting means so that the reference potential is impressed on it.

9. An apparatus for detecting within a generally uniform sheet material of extended length that moves along a path, a variation, such as a splice, in the otherwise uniform sheet material, said apparatus comprising: transmitting means for generating a sound along the path opposite one face of the moving sheet material; receiving means located along the path opposite the other face of the moving sheet material for converting the sound after it passes through the sheet and is attenuated thereby into an oscillating electrical signal of corresponding frequency, whereby the sound passing through the generally uniform portion of the sheet material will create within the oscillating signal a succession of peaks having a generally uniform magnitude, whereas the sound passing through the variation will create within the oscillating signal peaks of a different magnitude; amplifier means for amplifying the oscillating signal produced by the receiving means so as to provide an amplified signal likewise having peaks of a generally uniform magnitude representing the uniform portion of the sheet material and peaks of a different magnitude representing the variation; detector means for producing a generally constant reference potential which is less than the magnitude of the generally uniform peaks in the amplified signal; and comparing means connected to the amplifying means and the detector means for comparing the amplified signal with the reference potential and for indicating when the magnitude of the peaks in the amplified signal undergoes a change with respect to the reference potential, whereby the presence of a variation in the moving sheet material is detected, the comparing means producing a signal having a succession of pulses when the amplified oscillating signal constitutes a succession of uniform peaks and a discontinuity in the succession of uniform pulses when the magnitude of the peaks in the amplified signal undergoes a change.

10. The apparatus according to claim 9 whereas the reference potential produced by the detector means is proportional to the magnitude of the generally uniform peaks in the amplified signal irrespective of the magnitude of those uniform peaks.

11. The apparatus according to claim 10 wherein the detector means is connected to the amplifying means and converts the amplified signal into the reference potential.

12. In combination with a moving paper web having generally uniform thickness, but also having a splice of increased thickness, an apparatus for detecting the splice, said apparatus comprising: a transmit driver for producing first oscillating electrical signals at an ultrasonic frequency; a transmitter located opposite one face of the moving web and being connected to the driver, the transmitter converting the first electrical signal into ultrasonic sound of an intensity great enough to pass through the moving web, whereby the uniform web attenuates the sound and the splice will attenuate it still further; a receiver located opposite the other face of the moving web where the attenuated sound from the transmitter impinges on it, the receiver converting the ultrasonic sound into a second electrical signal which corresponds in frequency to the sound and has generally uniform peaks representing the sound attenuated by the uniform web and peaks of lesser magnitude representing the sound attenuated by the splice; amplifying means connected to the receiver for amplifying the second oscillating signal so as to produce a third oscillating signal which is an amplification of the second signal; detector means connected to the amplifying means for producing a reference potential which is less than the peaks of the third signal by a predetermined proportion; and comparing means for comparing the third signal with the reference potential and for indicating when the peaks of the third signal falls below the reference potential, thus denoting the passage of a splice between the transmitter and the receiver.

13. The combination according to claim 12 wherein the comparing means produces a fourth oscillating signal which contains a discontinuity when the magnitude of the peaks in the third signal fall below the reference potential.

14. The combination according to claim 13 and further comprising means for detecting discontinuities in the fourth signal.

15. The combination according to claim 12 wherein the driver is connected to the amplifying means and is sustained by the amplifying means.

16. The combination according to claim 12 wherein the transmitter and receiver are arranged such that a line extended between them is at an oblique angle with respect to the web in the direction of advance for the web.

17. The combination according to claim 12 wherein the detecting means comprises a first resistor, a diode and a capacitor connected in that order in series between a positive voltage source and a negative voltage source, with the anode of the diode being presented toward the resistor; an operational amplifier having positive and negative input terminals and an output terminal, the positive input terminal being connected to the amplifying means so that the third oscillating signal is impressed upon it, the negative input terminal being connected to the cathode of the diode and the output terminal being connected to the anode of the diode; and second and third resistors connected in series beyond the cathode of the diode, with the second resistor being connected between the cathode of the diode and the comparing means.

18. The combination according to claim 17 wherein the comparing means comprises an operational amplifier having a positive input terminal, a negative input terminal and an output terminal; and wherein the positive input terminal is connected to the amplifying means so that the third oscillating signal is impressed on it and the negative input terminal is connected to the second resistor of the detecting means so that the reference potential is impressed on it.

19. A process for detecting a splice in a web of otherwise uniform thickness, said process comprising: directing ultrasonic sound through the web from a fixed location as the web moves past that location, whereby the web attenuates the sound; receiving the sound after it passes through the web and converting the sound into a first oscillating electrical signal; amplifying the first signal to produce a second oscillating signal; converting the second oscillating signal into a reference potential which is a predetermined proportion of the amplitude of the peaks in the second signal irrespective of the amplitude of such peaks; comparing the second signal with the reference potential; and detecting when the amplitude of the peaks for the second signal falls below the reference potential, thus indicating the further attenuation of the sound as the result of a splice moving through the sound.

20. The process according to claim 19 wherein the step of detecting when the amplitude of the peaks falls below the reference potential comprises producing a third oscillating signal in response to the second signal when the second signal has peaks above the reference potential, and interposing a discontinuity in the third signal when the peaks fall below the reference potential.

21. The process according to claim 20 and further comprising using the second oscillating signal as a basis for producing the ultrasonic sound.

22. The process according to claim 19 and further comprising marking the web in response to the amplitude of the peaks in the second signal falling below the reference potential.

* * * * *

UNITED STATES PATENT OFFICE
CERTIFICATE OF CORRECTION

Patent No. 4,901,577　　　　　　　　　Dated　February 20, 1990

Inventor(s) CHRISTOPHER C. ROBERTS

It is certified that error appears in the above-identified patent and that said Letters Patent is hereby corrected as shown below:

Column 1, line 32, cancel "i" and substitute therefor "it".

Column 2, line 50, cancel "an" and substitute therefor "and".

Column 3, line 45, insert "6" after "driver".

Column 5, line 67, cancel "1 V" and substitute therefor --+1V--.

Column 10, line 22, cancel "peak-" and substitute therefor "peaks-".

Column 10, line 23, cancel "shaving" and substitute therefor "having."

Column 11, line 4, cancel "peak detector comprises" and substitute therefor "detecting means comprises".

Signed and Sealed this

Thirtieth Day of April, 1991

Attest:

HARRY F. MANBECK, JR.

*Attesting Officer*　　　*Commissioner of Patents and Trademarks*